(12) United States Patent
Borén et al.

(10) Patent No.: US 9,357,792 B2
(45) Date of Patent: Jun. 7, 2016

(54) FERMENTED CEREAL PRODUCT OBTAINED BY FERMENTATION OF RYE BRAN WITH A LACTOBACILLUS CURVATUS STRAIN

(75) Inventors: Thomas Borén, Umeå (SE); Göran Hallmans, Umeå (SE); Per Åman, Uppsala (SE)

(73) Assignees: Ingmar Borjesson, Jarma (SE); Leif Holmgren, Filipstad (SE)

( * ) Notice: Subject to any disclaimer, the term of this patent is extended or adjusted under 35 U.S.C. 154(b) by 1384 days.

(21) Appl. No.: 12/068,971

(22) Filed: Feb. 13, 2008

(65) Prior Publication Data

US 2009/0285794 A1    Nov. 19, 2009

Related U.S. Application Data

(63) Continuation of application No. 10/493,220, filed as application No. PCT/SE02/02036 on Nov. 7, 2002, now abandoned.

(30) Foreign Application Priority Data

Nov. 7, 2001 (SE) ..................................... 0103695

(51) Int. Cl.

| | |
|---|---|
| *A61K 36/899* | (2006.01) |
| *A23L 1/105* | (2006.01) |
| *A23K 1/00* | (2006.01) |
| *A23K 1/14* | (2006.01) |
| *A23K 1/175* | (2006.01) |
| *A23K 1/18* | (2006.01) |
| *A23L 1/10* | (2006.01) |
| *A23L 1/304* | (2006.01) |
| *A23L 2/52* | (2006.01) |
| *A61K 31/122* | (2006.01) |
| *A61K 33/26* | (2006.01) |
| *A61K 35/744* | (2015.01) |
| *A61K 35/747* | (2015.01) |
| *C12R 1/225* | (2006.01) |

(52) U.S. Cl.
CPC ................ *A23L 1/105* (2013.01); *A23K 1/007* (2013.01); *A23K 1/146* (2013.01); *A23K 1/1758* (2013.01); *A23K 1/184* (2013.01); *A23K 1/1813* (2013.01); *A23K 1/1826* (2013.01); *A23K 1/1846* (2013.01); *A23L 1/1016* (2013.01); *A23L 1/304* (2013.01); *A23L 2/52* (2013.01); *A61K 31/122* (2013.01); *A61K 33/26* (2013.01); *A61K 35/744* (2013.01); *A61K 35/747* (2013.01); *A61K 36/899* (2013.01); *C12R 1/225* (2013.01); *A23Y 2220/25* (2013.01)

(58) Field of Classification Search
None
See application file for complete search history.

(56) References Cited

U.S. PATENT DOCUMENTS

| | | | |
|---|---|---|---|
| 3,974,197 A | 8/1976 | Parliment | |
| 4,452,896 A | 6/1984 | Blakemore et al. | |
| 5,500,231 A * | 3/1996 | Buensow et al. | 426/18 |
| 5,578,302 A | 11/1996 | Brassart et al. | |
| 5,587,314 A | 12/1996 | Bengmark et al. | |
| 5,879,729 A | 3/1999 | King Solis et al. | |
| 6,066,373 A | 5/2000 | Floyd, Jr. et al. | |
| 6,203,835 B1 * | 3/2001 | Westermarck et al. | 426/335 |

FOREIGN PATENT DOCUMENTS

| | | |
|---|---|---|
| EP | 04-063587 | 2/1992 |
| EP | 06-098782 | 12/1994 |
| EP | 1 034 787 A1 | 9/2000 |
| EP | 1034787 A1 | 9/2000 |
| WO | 90/09398 A1 | 8/1990 |
| WO | 9009398 A1 | 8/1990 |
| WO | WO 97/00018 | 1/1997 |
| WO | 9918188 A1 | 4/1999 |
| WO | WO00/75142 A2 | 12/2000 |
| WO | 0110448 A1 | 2/2001 |

OTHER PUBLICATIONS

Muller et al. (International J. of Syst. and Evol. Microbiol., (2000), 50, 2127-2133).*

Coenen et al.., 2001: Fermented rye bran—an interesting ingredient and an example for a significant technology. Landbauforschung Volkenrode, Sonderheft ( 223): 259-263.*

Cover, T.L., Berg, D.E., Blaser, M.J., and Mobley, H.L.T. (2001), "*H. pyloh* pathogenesis. In Principles of bacterial pathogenesis", E. A. Groisman, ed. (New York, Academic Press), pp. 509-558.

H. Clausen and S. Hakomori, 1989, *Vox Sang*, 56, 1-20.

T. Boren, P. Falk, K.A. Roth, G. Larson and S. Normark, "Attachment of Helicobacter pylori to human gastric epithelium mediated by blood group antigens", *Science*. 262, 1892, 1993.

D. Iiver, A. Arnqvist, J. Ogren; I.M. Frick, D. Kersulyte, E.T. Incecik, D.E. Berg, A. Covacci, L. Engstrand and T. Boren, "H. pylori Adhesin Binding Fucosylated Histo-Blood Group Antigens Revealed by Retagging", *Science*, 279, 373-377, 1998.

(Continued)

*Primary Examiner* — Irene Marx

(74) *Attorney, Agent, or Firm* — Bacon & Thomas, PLLC

(57) ABSTRACT

The present invention refers to a non-antibiotic therapeutic strategy for inhibiting oro-gastro-intestinal infections and pathogens in general and particularly *Heliobacter pylori* adherence and colonization in the gastrointestinal channel and preventing or relieving associated oro-gastro-intestinal disease. The invention relates to methods and products based on an active cereal product or ferric quinate. The invention is also applicable to other oro-gastro-intestinal pathogens in both humans and animals.

4 Claims, 11 Drawing Sheets

(56) References Cited

OTHER PUBLICATIONS

M. Gehard, N. Lehn, N. Neumayer, T. Boren, R. Rad, W. Schepp, S. Miehlke, M. Classen and C. Prinz, "Clinical relevance of the Helicobacter pylori gene for blood-group antigen-binding adhesin", *Proc. Natl. Acad. Sci* USA, 96, 12778-12783, 1999.

H. Miyabayashi, K. Furihata, T. Shimizu, I. Ueno, T. Akamatsu, "Influence of oral Helicobacter pylori on the success of eradication therapy against gastric Helicobacter pylori", Helicobacter, 5, 30-37, 2000.

M. Sadaka and A. Garcia, "Extraction of skimic and quinic acids", *Chem. Eng. Comm.* 173, 91-102, 1999.

P. Falk, K.A. Roth, T. Boren; T.U. Westblom, J.I. Gordon and S. Normark, "An in vitro adherence assay reveals that Helicobacter pylori exhibits cell lineage-specific tropism in the human gastric epithelium", *Proc. Natl. Acad. Sci.* U.S.A., 90, 2035, 1993.

Cooper H.S., Murthy S.N.S., Shah R. S. and Sedergran D.J. (1993): Clinicopathologic study of dextran sulfate sodium experimental murine colitis. *Lab. Invest.* 69:238-249.

Mahler M., Bristol I.J., Leiter E.H., Workman A.E., Birkenmeier E.H., Elson C.O. and Sundberg J.P. (1998): Differential susceptibility of inbred mouse strains to dextran sodium-induced colitis. *Am. J. Physiol.* 274:G544-551.

Okayasu I., Hatakeyama S., Yamada M., Ohkusa T., Inagaki Y. and Nakaya R. (1990): A novel method in the induction of reliable experimental and acute chronic ulcerative colitis in mice. *Gastroenterology* 98:694-702.

Scand J Gastroenterol, vol. 30, 1995, X.D. Wang et al., "The Role of Oral Administration of Oatmeal Fermented by Lactobacillus Reuteri R2LC on Bacterial Translocation after Acute Liver Failure Induced by Subtotal Liver Resection in the Rat", pp. 180-185.

BIOSIS, accession No. PREV199800184380, Rani Binita et al., "Probiotic fermented food mixtures: Possible applications in clinical anti-diarrhoea usage", Nutrition and Health (Bicester), 1998, vol. 12, No. 2, pp. 97-105.

International Dairy Journal, vol. 8, No. 5-6, 1998, M.R.A. Muller et al:"Adhesion of Lactobacillus Strains from Cereal Fermentations to Human Intestinal Cells", p. 584.

BIOSIS, accession No. PREV199698694233, Binita N. Khetarpaul et al., "Development, acceptability and nutritional composition of food blends fermented with probiotic organism", Annals of Biology (Ludhiana), 1996, vol. 12, No. 1, pp. 127-133.

PNAS, vol. 96, No. 22, Oct. 1999, Markus Gerhard et al., "Clinical relevance of the Helicobacter pylon gene for blood group antigen-binding adhesion", pp. 12778-12783.

Chem. Eng. Comm., vol. 173, 1999, Mariam Sadaka et al., "Extraction of shikimic and quinic acids", pp. 91-102.

European Communication in corresponding European Application No. 02 786 306.7, dated Sep. 5, 2012.

\* cited by examiner

Inhibition of *H. pylori* adherence to gastric epithelium, *In Situ*, by pre-treatment with fermented rye bran or Ferric Quinate Control     *L. curvatus* -fermented- rye bran     Ferric Quinate Quantification of *H. pylori* adherence to gastric epithelium, *In Situ*

I: Lewis b conjugate
II: *L. curvatus* -fermented-rye bran
III: Ferric Quinate

-R: reduction in binding

Inhibition of *H pylori* binding to the Lewis b antigen by pre-treatment with heat-treated fermented rye bran (analyzed by RIA)

Inhibition of *H pylori* to the Lewis b antigen by pre-treatment with various fermented cereals (analyzed by RIA)

Treatment of human volunteers with drinkable fermented rye bran product iBran™

FERMENTED CEREAL PRODUCT OBTAINED BY FERMENTATION OF RYE BRAN WITH A LACTOBACILLUS CURVATUS STRAIN

CROSS-REFERENCE TO RELATED APPLICATIONS

This application is a divisional of patent application Ser. No. 10/493,220, filed May 6, 2004 as the national stage of PCT/SE02/02036, filed Nov. 7, 2002.

FIELD OF THE INVENTION

The present invention refers to a novel preventive and therapeutic strategy for combating disorders caused by pathogenic microorganisms in the human and animal oro-gastrointestinal tract. It is a treatment against mucosal infectious pathogens in humans, e.g. *Helicobacter pylori*, *Streptococcus mutans* and *Candidia albicans*, based on an activated cereal product. It is also a treatment against microbial enteric pathogens, such as *Escherichia coli* and *Clostridium perfringens*, in the gastro-intestinal tract of domestic animals such as in cattle, pig and chicken and, in addition, in pet animals such as dogs and cats. In addition, the invention also comprises the fermentation process producing this active product. The invention further refers to the functional food area, as the activated cereal product is presented to the patient as a palatable food or beverage product. Furthermore, the invention refers to supplemental growth promoting active feeding-stuff supplement for animals such as pigs and chickens.

BACKGROUND OF THE INVENTION

*Helicobacter pylori*, a human specific gastric pathogen, colonizes the human gastric mucosa and the consequence is a higher prevalence of gastric diseases, such as chronic active gastritis and peptic ulcer disease. In the industrialized world, less than 20% of young people are infected, increasing to about half the population by 50 years of age. *H. pylori* has adapted to the hostile and acidic environment of the human stomach. Peristalsis and the high turnover rate of mucus and epithelial cells pose serious obstacles for microbes that strive to retain a niche in the gastric epithelial lining. Here, *H. pylori* can establish a protected niche for survival and long-term colonization of the gastric mucosa. Once established in the host, the bacteria can persist for the lifetime of the host. Chronic infection has been correlated to the development of gastric adenocarcinoma, one of the most common forms of cancer in humans (reviewed in Cover et al, 2001). Interestingly, most infected individuals show no clinical symptoms, implying the influence of additional factors in the pathogenesis of the disease such as diet, genetic predisposition, age of acquisition of the infection, and the genotype of the infecting strain.

*H. pylori* colonizes the human gastric mucosa by adherence both to the mucous epithelial cells and to the mucus layer lining the gastric epithelium. *H. pylori* demonstrates various adhesion properties for adherence to the mucus layer and the epithelial cell glycoproteins and glycolipids. The microbial affinity for specific receptor structures, in combination with unique tissue-specific distribution of receptors, will restrict the colonization to the gastric/duodenal mucosa. The *H. pylori* adherence to the fucosylated blood group antigens Lewis b and H-1, (described by Clausen, et al, 1989) in human gastric mucosa has been demonstrated (Borén, et al, 1993). Recently the cognate *H. pylori* blood group antigen binding adhesin, BabA, was identified (Ilver, et al., 1998). A panel of 95, clinical isolates was analyzed for Lewis b antigen binding properties. The majority of the isolates, 66%, were found positive for binding, demonstrating the high prevalence of blood group antigen binding activity among clinical isolates (Ilver, et al., 1998). By epidemiological screening, the Lewis b antigen binding property was found prevalent among the virulent strains that carry the cagPathogenicity Island and the vacuolating cytotoxin, i.e. the triple-positive strains. It is therefore proposed that Lewis b antigen mediated adherence of *H. pylori* play a critical role for development of severe gastric disease (Gerhard, et al., 1999).

The International Patent Application No. PCTVSE97/01009, published as WO97/47646, relates to the *Heliobacter pylori* adhesin binding group antigen.

An investigation of the influence of oral *H. pylori* on the success of eradication therapy suggests that the presence of oral *H. pylori* is an important factor for gastric infection (due to the numbers of patients who proved to be recurrent or refractory after eradication therapy). The most plausible explanation would be that these patients were infected with *H. pylori* in the oral cavity and dental plaques (Miyabayashli, et al, 2000), which suggests that *H. pylori* infections should be eradicated.

From U.S. Pat. No. 5,633,244, it is known to treat gastritis and peptic ulcer caused by *H. pylori* by administration of an acid degradable antibacterial compound in combination with a histamine-$H_2$ receptor blocking compound. The acid degradable antibacterial compound can also be used in combination with a proton pump inhibitor such as omeprazole and lansoprazole (U.S. Pat. No. 5,629,305). The antibacterial compound is a penicillin, such as benzylpenicillin, or a macrolide, such as erythromycin.

The increased antibiotic resistance among virulent bacterial strains is a major cause for the development of alternative anti-microbial strategies, such as functional food strategies. Detailed knowledge about the mechanisms which support the adherence processes of *H. pylori* is vital for the development of alternative anti-microbial strategies, such as the invention described and claimed for in the present pending application.

BRIEF DESCRIPTION OF THE INVENTION

The object of the invention is to provide a non-antibiotic therapeutic alternative against *H. pylori* infection in the human gastro-duodenal-tract and, in addition, a non-antibiotic therapeutic alternative against oro-gastro-intestinal-disease in both humans and in animals. The object of the invention is attained by using activated product/products from a fermented cereal product, and a purified compound, Ferric Quinate (Fe-QA) which, as a natural component of the biomass, is soliubilized during the fermentation process. The effect of the active product is an inhibition of *H. pylori* adherence and colonization in the human gastrointestinal tract. This effect could protect against *H. pylori* and other pathogens such as *Candida albicans* and *Streptococcus mutans* and thus, reduce the risk of oro-gastro-intestinal disorders in humans and, in addition, protect against microbial-enteric pathogens such as *Escherichia coli* and *Clostridium perfringens*, in the gastro-intestinal tract in farming animals and pets. The preferred embodiment is an activated rye-bran product (i-Bran™) from the supernatant of a cell culture of *Lactobacillus curvatus*-fermented rye-bran. The rye-bran product is presented to the patient in the form of a palatable beverage or food product. Alternatively, the product is used for preventive or therapeutic treatment of domestic cattle, pig and chicken

Human buccal epithelial cells were first treated with parotid saliva (diluted 1:1 with PBS buffer), and then 35S-labeled *Candida albicans* cells were added.

Figure 7A:
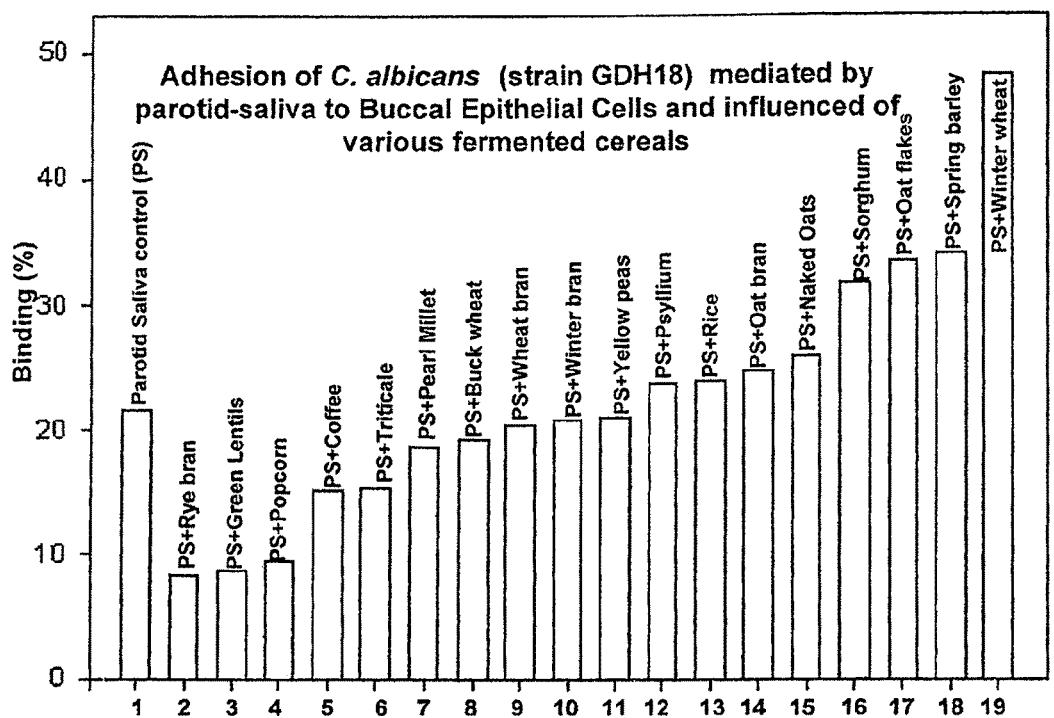
FIG. 7A shows adhesion of *C. albicans* strain GDH18) mediated by parotid-saliva to buccal epithelial cells and influenced of various fermented cereals.
Figure 7B:
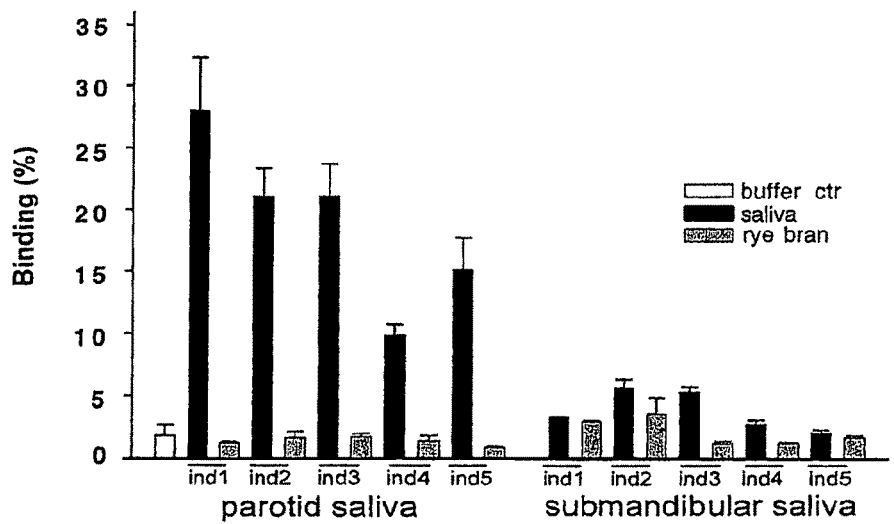

FIG. 7B shows adhesion of *Streptococcus mutans* to saliva-treated hydroxy-apatite and the reduction in binding conferred by the rye bran product.

FIG. 8 shows comparison of clinical symptoms between mice exposed to DSS or a mixture of DSS and the fermented rye product. Both groups loose weight at a similar rate (A and B). The mortality of the mice in both groups is similar and divergence of the curves is due to the relatively small number of mice analyzed (C). Both groups show gross bleeding as a sign of epithelial damage (D) but the mice exposed to the fermented rye product clearly display less intestinal symptoms such as loose stools and diarrhea (E and F).

Figure 9:
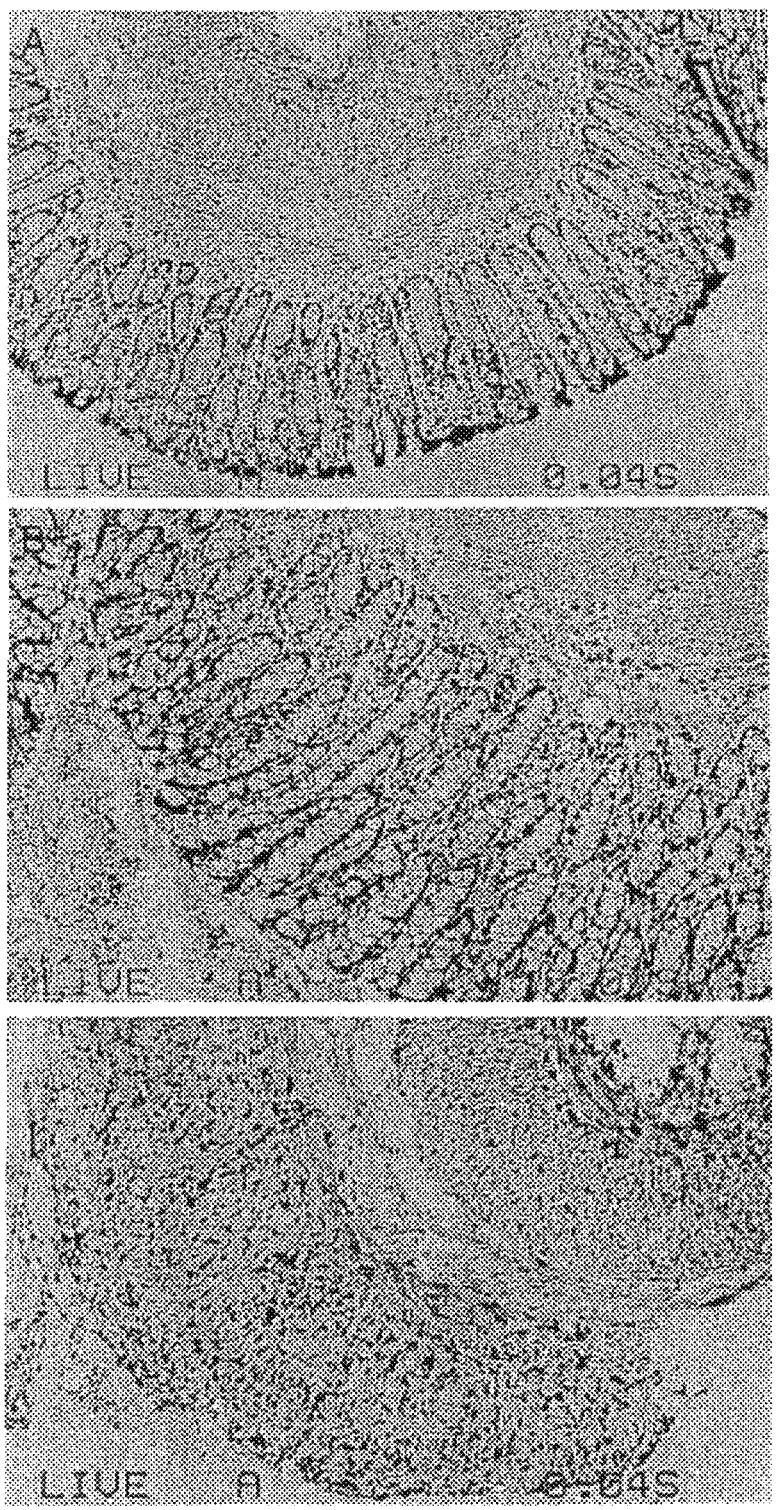

FIG. 9 shows comparison of histology of an untreated control (A), a mouse exposed to a mixture of DSS and the fermented rye product (B) and a mouse exposed to only DSS (C). Epithelial damage can be observed in both groups of mice exposed to DSS (B and C), but the inflammation is more severe in the mice exposed to DSS only (C) when compared to the mice exposed to a mixture of DSS and the fermented rye product (B).

DETAILED DESCRIPTION OF THE INVENTION

The present invention is based on the surprising discovery that the colonization of *Helicobacter pylori* (*H. pylori*) in the human gastrointestinal channel and other oro-gastro-intestinal pathogens (OGIP) in humans and animals are inhibited by certain fermentation products derived from a cereal upon fermentation of the same.

Thus, according to a first aspect, the invention relates to a cereals fermenting microorganism having the ability to provide, upon fermentation of the cereal, activated products derived from the cereal and being competetive inhibitors of the adherence and colonization of OGIP in humans and animals, particularly *H. pylori* in humans.

It is preferred to use, as a cereals fermenting microorganism, a *Lactobacillus* bacterial strain, and in particular a *Lactobacillus curvatus* (*L. curvatus*) strain. According to the preferred embodiment use is made of the *L. curvatus* strain Lb14 which has been deposited, under the terms of the Budapest Treaty, at Deutsche Sammlung von Mikroorganismen and Zeilkulturen GmbH (DSMZ) on Dec. 7, 2000 and having received the accession number DSMZ 13890.

The Lb14 strain used forms small white colonies on "Rogosa SL Agar BBL" plates which is typical for *Lactobacillus* strains. This strain was originally isolated from human urine and identified as *Lactobacillus curvatus* by use of the "API-50, CHL" test.

OGIP infections other than infections by *H. pylori* to be treated are infections by *Candida albicans*, and dental pathogens, such as *Streptococcus mutants*, in humans and *Escherichia coli* and *Clostridium perfringens* in domestic animals, e.g. cattle, pig and poultry; and pets, e.g. dogs and cats.

It has here also been shown that the fermented cereal product of the invention also has the ability to block the adhesion of the "dental caries" bacterium *Streptococcus mutans* to saliva-covered hydroxyl apatite (HA), i.e. the material of the tooth surfaces.

In order to establish whether a microorganism has the ability to provide, upon fermentation of a cereal, fermentation products being competetive inhibitors of the colonization of e.g. *H. pylori* in the human gastro-intestinal channel, use can be made of the methods described in the Experimental Section to follow, Examples 4 and 5.

During the fermentation process active components from the cereal product are released because of *Lactobacillus* enzymatic processes. These components are responsible for the inhibiting activity on *H. pylori* colonization. Cf. Example 6 in the Experimental Section below.

Although it is likely, that the same enzymatic processes produce identical or similar active components in many different cereal products upon fermentation of the same, the preferred embodiment of the invention uses rye bran as cereal product for the fermentation.

According to a second aspect, the present invention relates to a fermented cereal product being obtained by fermentation of a cereal with a microorganism of the invention and being a competetive inhibitor of the colonization of OGIP in humans and animals.

The preferred embodiment of this aspect is an active rye bran product (iBran™) being the supernatant from the fermentation broth obtained when fermenting rye bran by *L. curvatus* Lb14 (DSMZ 13890). It has been found to act as an inhibitor of *H. pylori* colonization in the human gastrointestinal channel. A component/components in the active rye bran product (iBrant™) prevents the adhesion of *H. pylori* to the gastric mucosa and epithelial lining by inhibiting the binding between BabA (blood group antigen binding adhesion) on the surface of *H. pylori* and the fucosylated Lewis b antigen on the gastric epithelial surface. These inhibitory properties against *H. pylori* adherence were analyzed experimentally in vitro, in situ and in vivo (cf. the Experimental Section below). In addition, the inhibitory properties against *Candida albicans* adherence was analyzed experimentally by saliva coated buccal epithelial cells (example 9, FIG. 7A), as well as the inhibitory properties against *Streptococcus mutans* adherence which was analyzed experimentally by saliva-coated hydroxyl apatite (HA) (Example 9, FIG. 7B).

According to a third aspect, the present invention relates to the use of a fermented cereal product of the invention for the preparation of a functional food product having the property, upon consumption of the same, of competetively inhibiting the colonization of OGIP in humans and animals, particularly *H. pylori* in the human gastrointestinal channel.

The preferred embodiment of this third aspect is the use of the supernatant of the fermentation broth obtained by fermentation of rye bran by the *L. curvatus* strain Lb14 (DSMZ 13890).

A fourth aspect of the present invention relates to a functional food product being useful for treatment of humans and animals suffering from OGIP infections and particularly humans suffering from *H. pylori* infections and associated gastric disease.

The preferred embodiment of this fourth aspect is a functional food product comprising the supernatant of the fermentation broth obtained by fermentation of rye bran by the *L. curvatus* strain Lb14 (DSMZ 13890).

The fermented rye bran product, preferably the supernatant of its fermentation broth, is mixed with other ingredients to form a palatable food product, e.g. a beverage, bread or muesli. A preferred embodiment is to add 10% lingonberry juice and 10% glucose to form a tasty beverage. Ninety liter of the supernatant obtained from the fermented rye (in accordance to protocol below) was mixed with 10 kg glucose (Sigma, St. Louis, Mo., USA), and 10 liter of lingonberry juice (from 17 kg cool pressed berries). The treatment dosage is 10-500 mL product, preferable 100 mL, taken 1-5 times a day, preferable three times daily, which corresponds to 10-2.500 mL fermented rye-bran per day, preferable 300 mL.

A fifth aspect of the present invention relates to a method of preparing a fermented cereal product by subjecting, under conditions suitable for providing fermentation products from the cereal being competetive inhibitors of the colonization of OGIP in humans and animals, particularly *H. pylori* in the human gastro-intestinal channel, the cereal to fermentation by a microorganism of the invention and collecting the product from the fermentation broth.

The active substance or substances of the fermented cereal product may be concentrated or isolated by the use of different methods, such as selective extraction, precipitation, ultra-filtration, enzymatic treatment or chromatography.

The preferred embodiment of the method comprises subjecting rye bran to fermentation by the *L. curvatus* strain Lb14 (DSMZ 13890). In the preferred method, the bacterial cells and rye bran are incubated at 37° C. for about 24 hours.

A further aspect of the present invention relates to pharmaceutical products based on purified extracts, or fraction of extracts, and/or ferric quinate, with the *Helicobacter pylori*—Lewis b antigen binding inhibitory (blocking) activity as a marker for the activated inhibitor of the invention, for treatment of humans suffering from oro-gastro-intestinal pathogens infections in humans and domestic animals, such as for treatment of *Helicobacter pylori, Candida albicans* och *Streptococcus mutans* infections in humans and for treatment of *Escherichia coli* and *Clostridium perfringens* infections in domestic cattle, pig and poultry.

A particular embodiment relates to a pharmaceutical product in the form of a mouth rinse for treatment of dental caries, periodontal disease and oral malodor/halitosis.

A further particular embodiment relates to treatment of human intestinal inflammation, such as ulcerative colitis and Crohn's disease, with a fermented rye bran product.

The present invention is further illustrated by the non-limiting Examples to follow in the Experimental Section below.

EXPERIMENTAL SECTION

Description Of Preferred Embodiment

This section describes the process for fermentation of rye-bran, the preferred activated cereal product and characterization of the activated cereal product effect, preferably the rye-bran effect on *Helicobacter pylori* adhesion and *Candida albicans* adhesion.

Example 1

Growth of *Lactobacillus curvatus*, Lb14

For fermentation of rye bran, *Lactobacillus curvatus* (*L. curvatus*) Lb14 was grown in MRS broth (Difco) at 37° C. with gentle shaking for 24 hours.

Example 2

Process for Fermentation of Rye-Bran

One gram of rye-bran (Nordmills, Uppsala) was suspended in 10 mL distilled water and 1:1000× of *L. curvatus* culture (see above) was mixed to form the fermentable rye-bran suspension. The fermented suspension of bacterial cells and rye-bran was then incubated in 37° C. with gentle shaking for 24 hours in normal atmosphere. The material was then pelleted and thus, cleared, through centrifugation for 10 min at 10.000 rpm. For long-term storage and for use in clinical trials, the supernatant was autoclaved for 20, min, at 120° C., aliquoted and stored at −20° C. (see below and FIG. 4).

Example 3

*H. pylori* Strain and Growth Conditions

Strain CCUG17875 (cag+, vacuolating toxin+) was obtained from the Culture Collection University of Goteborg (CCUG), Sweden. Bacteria was cultured from frozen stock onto the media containing "Brucella" agar (Eifco, U.S.) supplemented with 10% bovine blood, "IsoVitox Enrichment" (Svenska LabFab, Sweden) at 37° C. under microaerophilic condition for 2 days. Bacterial cells were harvested and washed in PBS 2 times. Then the cells were re-suspended to a density of $1 \times 10^8$ CFU/mL in PBS for analyzes of the biological effects of the activated rye-bran product.

Example 4

Inhibition Assay with Fermented Rye Bran by Using Radio Labeled Semi-Synthetic Glycoprotein, Lewis b The Lewis b blood group antigen used was semi-synthetic glycoprotein constructed by covalent binding of purified Lewis b oligosaccharide to human serum albumin (IsoSep AB, Tullinge, Sweden). The RIA assay was performed according to Ilver et al., 1998; The Lewis b conjugate was 125I-labeled by the "Choramine" method as used in Ilver et al., 1998. Briefly, 1 mL of bacteria at an optical density of A600;OD=0.10) was incubated with 300 ng of 125I-labeled Lewis b conjugate for 2 hours in phosphate buffered saline (PBS), 1% albumin, 0.05% "Tween 20" (blocking-buffer, (denoted BB)). After centrifugation, Lewis b conjugate bound to the bacterial pellet was measured by gamma scintillation counting in the bacterial pellet. For analyzes of bacterial binding inhibitory activities, bacteria were either pre-treated or post-treated with L. curvatus-fermented rye-bran product to analyze for inhibitory activities towards the bacterial binding properties.

Figure 1A:
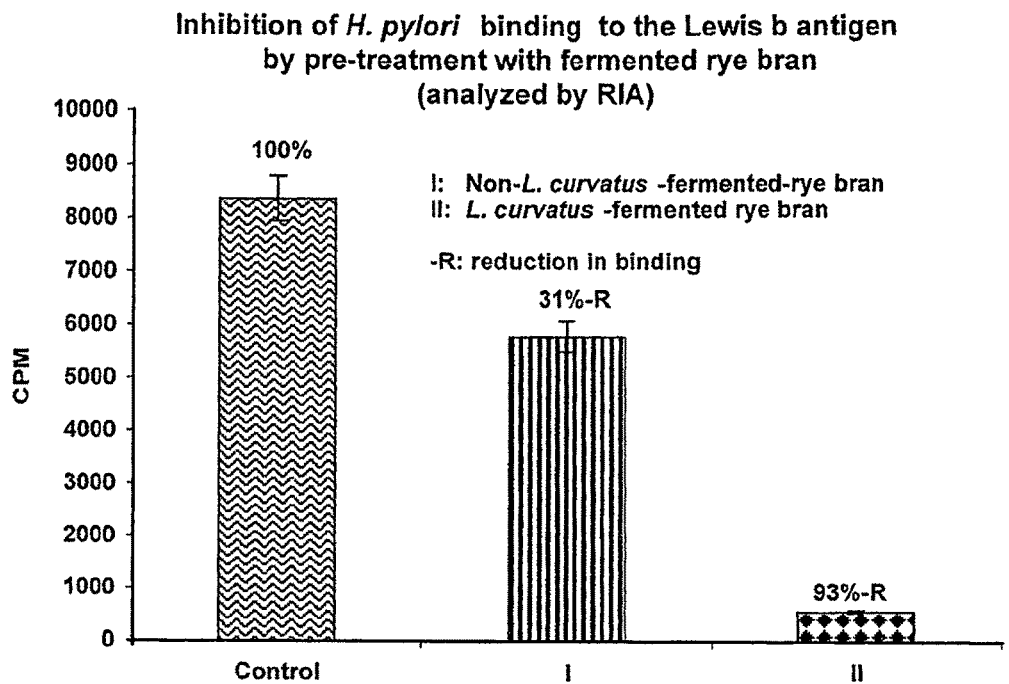
FIG. 1A shows an inhibition assay with strain *H. pylori* CCUG17875,, pretreated with fermented rye-bran for 1 hour and then analyzed for binding to 125I-labeled Lewis b conjugate. The rye-bran products used for the bacterial binding experiments are given in the figure and the bars give the corresponding bacterial binding. The bars: I: rye-bran, II: rye-bran fermented by *L. curvatus*. The percentage of reduction in binding is given in the figure.
Figure 1B:
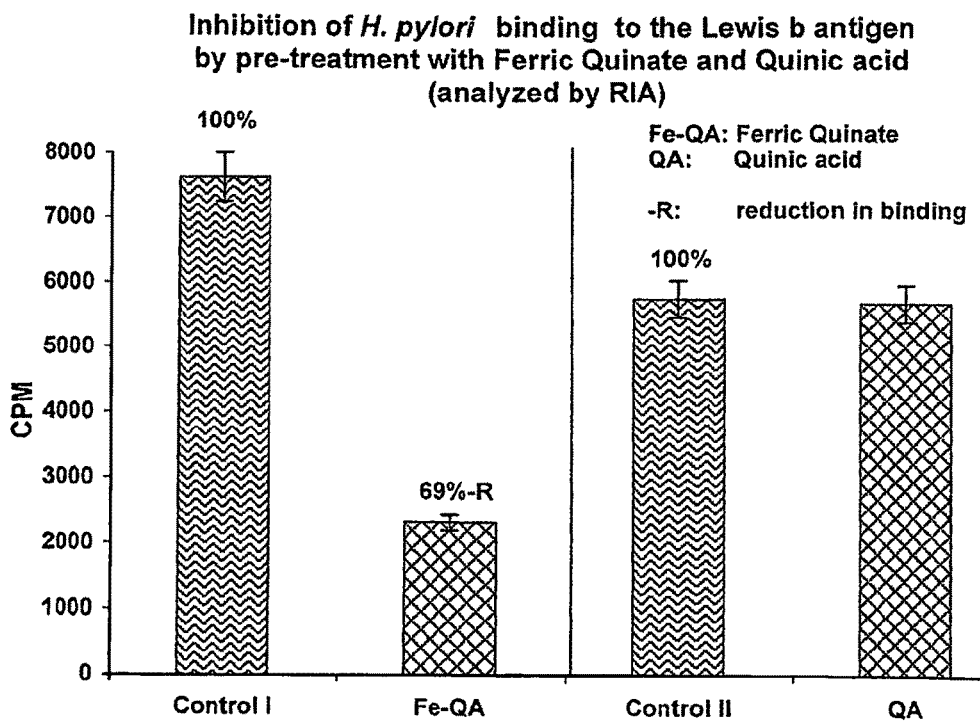
FIG. 1B shows an inhibition assay with strain *H. pylori* CCUG17875, pretreated with 2 mM ferric quinic acid (Fe-QA) for 1 hour and then analyzed for binding to 125 I-labeled Lewis b conjugate. Pre-treatment with 2 mM (non-ferric) quinic acid (QA) is also shown. Both experiments are shown together with their corresponding non-treated control (Control I and II, respectively)

The inhibitory potential of fermented rye-bran product on adherence of H. pylori was analyzed by RIA assay using radiolabeled Lewis b antigen. H. pylori (as described above) was pre-incubated with 1 mL L. curvatus-fermented rye-bran products which resulted in >90% inhibition of binding to the Lewis b antigen (FIG. 1A). In contrast, the non-L. curvatus-fermented rye bran product provides merely 31% reduction in binding of H. pylori. The results also showed that the activated compound with an inhibitory effect on bacterial binding is released due to the fermentation process. It has been mentioned that Quinic Acid and other shikimic acid derivatives and metabolites can be formed during fermentation of biomass (Sadaka and Garcia, 1999). In this invention Ferric Quinate (Fe-QA) conferred a 69% inhibition of binding, while Quinic Acid (QA) provided no inhibition of H. pylori binding (FIG. 1B).

Figure 2:
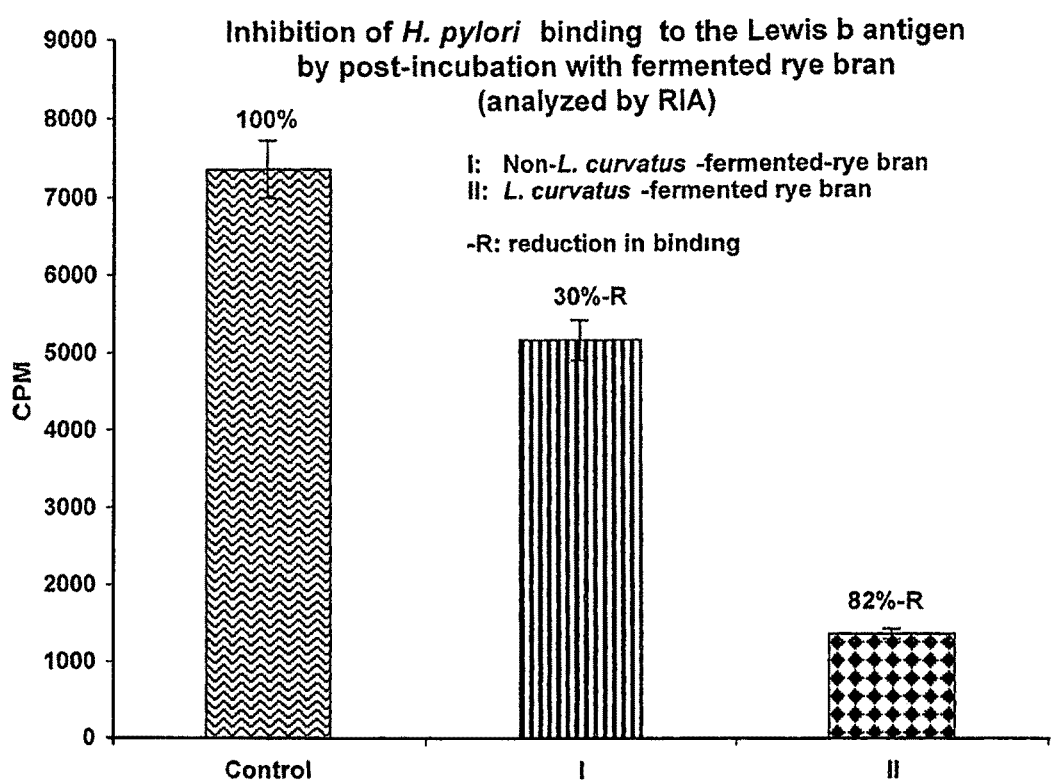
FIG. 2 shows an inhibition assay where strain *H. pylori* CCUG17875 was first incubated with the 125I-labeled Lewis b conjugate for 2 hours to allow for full binding. The *H. pylori* cells were then incubated with rye-bran products for an additional 2 hours to analyze for detachment of bacterial binding. The reduction of the binding of a non-*L. curvatus*-fermented rye-bran product is also shown. The bars: I: rye-bran, II: rye-bran fermented by *L. curvatus*.

Specific inhibition was also analyzed by post-treatment with L. curvatus-fermented rye-bran of H. pylori with bound Lewis b conjugate. The results from the post-treatment approach also demonstrated the importance of the fermentation process to achieve reproducible inhibition of microbial adherence. L. curvatus-fermented rye-bran products reduced bacterial binding by performing 60-80% of bacterial detachment. In contrast, non-L. curvatus-fermented rye-bran had less effect on bacterial binding (FIG. 2).

Example 5

Figure 3A:
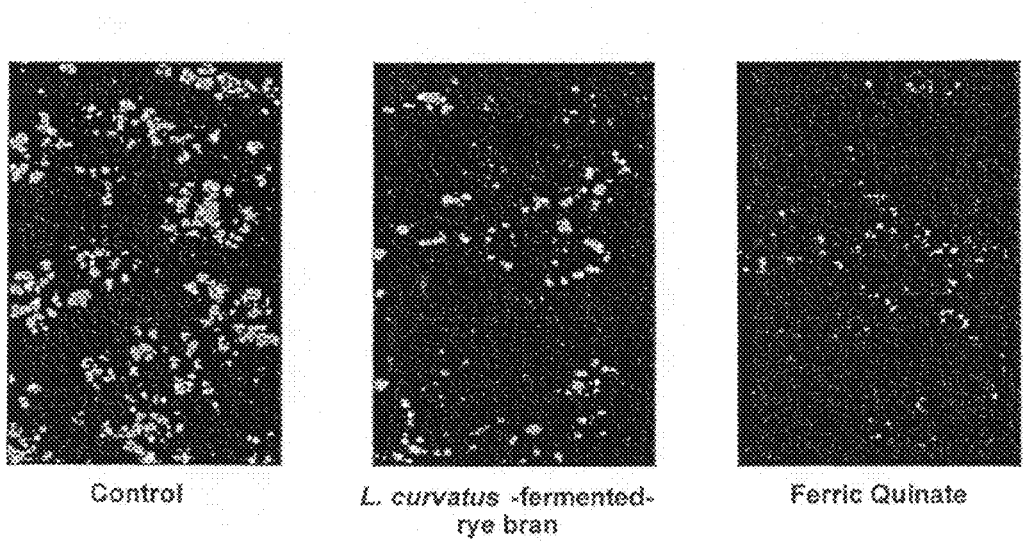
FIG. 3A shows in vitro adherence analysis of *H. pylori* binding to histo-sections of human gastric mucosa, and the effect of bacterial pre-treatment with fermented rye-bran and 2 mM ferric quinic acid.
Figure 3B:
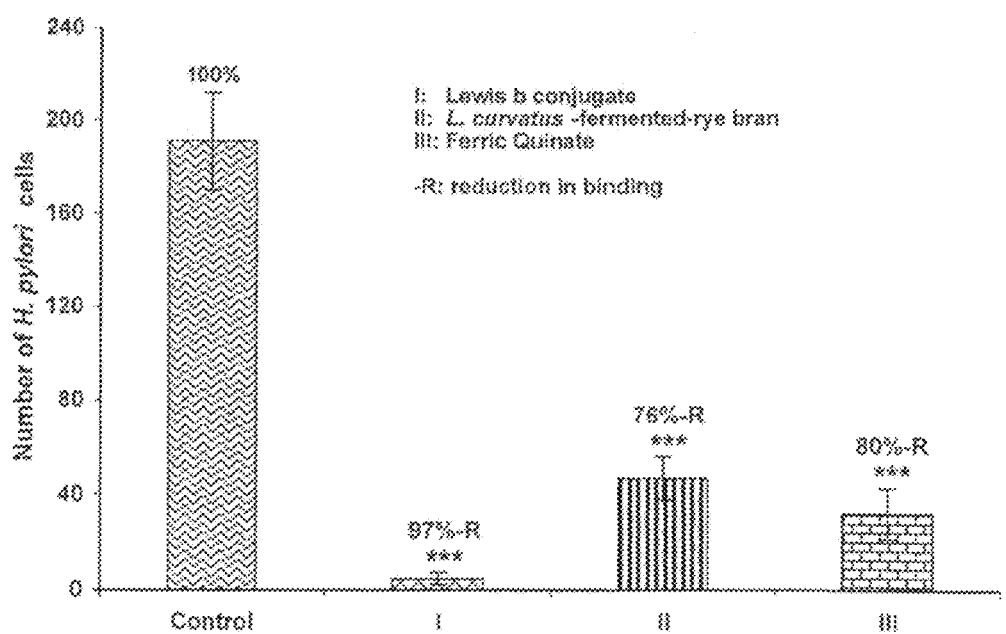
FIG. 3B shows the quantification of remaining *H. pylori* attached to the histo-sections of human gastric mucosa. Pretreatment of strain CCUG 17875 with soluble Lewis b antigen, with *L. curvatus* fermented rye bran and with ferric quinate is shown. Here, bacterial binding to 10 different gastric surface epithelium regions were estimated (value $p<0.001$(*), value $p<0.01$(), value $p<0.05$(*)).

H. pylori Adherence in situ and Inhibition of Binding by use of the Fermented Rye-Bran Product Bacterial adherence in situ was performed as described by Falk et al., 1993. Human biopsy samples of healthy gastric tissue were obtained from the Division for Gastroenterology, Norrland University Hospital, Umea, Sweden. The biopsies were taken from the antrum part of the stomach, then they were fixed in 4% buffered formalin and finally they were embedded in paraffin wax. Sections were stained with hematoxylin and eosin following standard procedures. H. pylori were first labeled with FITC, and bacterial adherence to the gastric mucous was then analyzed by the ability of L. curvatus-fermented rye-bran to inhibit bacterial adherence to re-hydrated histo-sections of human gastric epithelial cells in situ. For comparative inhibition analyzes, H. pylori was pre-incubated with Lewis b conjugate (10 µg/mL), and fermented rye-bran (1 mL) for 1 hour at room temperature. Then, as described above, the H. pylori bacterial cells were applied to the histo-sections. Pretreatment of strain H. pylori CCUG17875 with the L. curvatus-fermented rye-bran product prevented adherence (>75% reduction) to the human gastric mucosa, in situ. Thus, a reverse correlation between H. pylori pre-incubated with L. curvatus-fermented rye-bran product and untreated H. pylori attached to the gastric cells was demonstrated (FIGS. 3A and 3B).

Reduction in bacterial binding was estimated by counting the number of specifically adhered bacteria to the gastric pit region under 200 x magnification. Each value is the mean +/- SEM of 10 different fields. In the control experiments, bacteria were not preincubated with neither Lewis b conjugate, nor fermented rye-bran, and that was defined as 100% binding reference. Student's t-test was used to assess the significance of differences between means in non-inhibited binding and inhibition analyses.

To summarize, the following was confirmed:
Strain H. pylori CCUG17875 adheres efficiently to the gastric epithelium in vitro (untreated control).
Adherence of strain CCUG17875 to the gastric tissue section epithelium after pretreatment with the L. curvatus-fermented rye-bran product was much reduced Adherence of strain CCUG17875 to, the gastric tissue section-epithelium after pretreatment with 2 mM Ferric Quinic Acid (Fe-QA) was similarly much reduced.

Example 6

Inhibition Effect of Heat-Treated Fermented Rye-Bran on H. pylori Adherence

Figure 4:
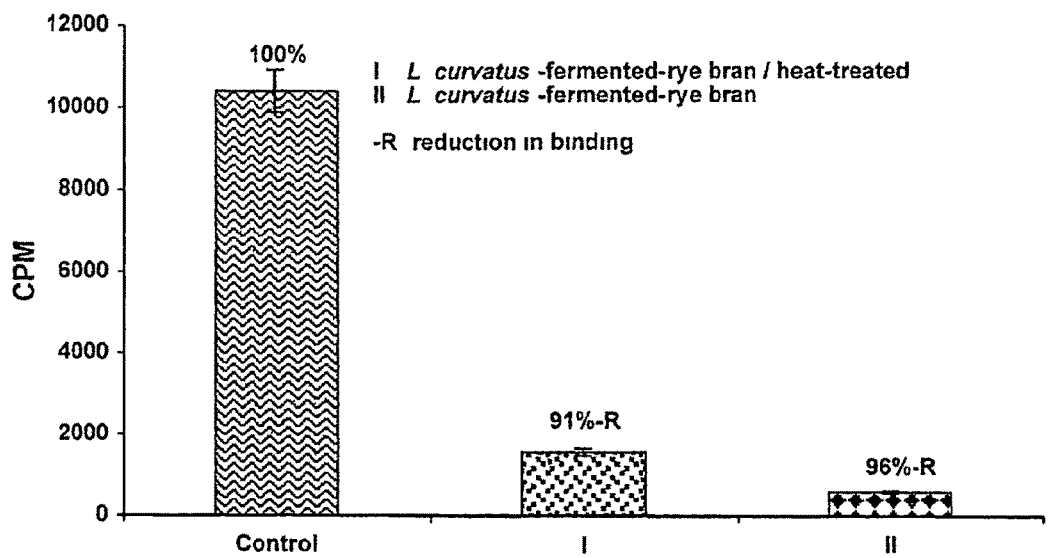
FIG. 4 shows inhibition of *H. pylori* binding to the Lewis b antigen by pretreatment with heat-treated fermented rye bran (analyzed by RIA). The fermented rye-bran was boiled 100° C. for 3 hours. The volume of heat-treated product was then adjusted for the subsequent analyzes of inhibition activity. The reduction of *H. pylori* CCUG17875 binding was measured as described in FIG. 1.
Figure 5:
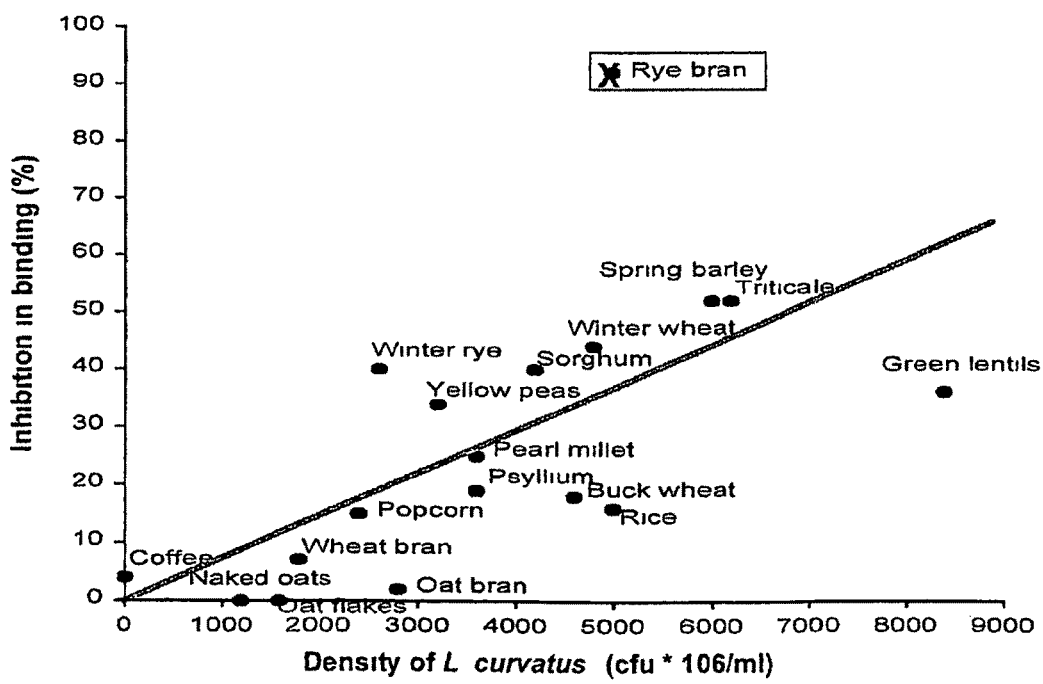
FIG. 5 shows inhibition of *H. pylori* binding to the Lewis b antigen by pretreatment with various fermented cereals (analyzed by RIA). Several cereals (seeds and seed fractions) were studied for inhibition of *H. pylori* binding.
Figure 6A:
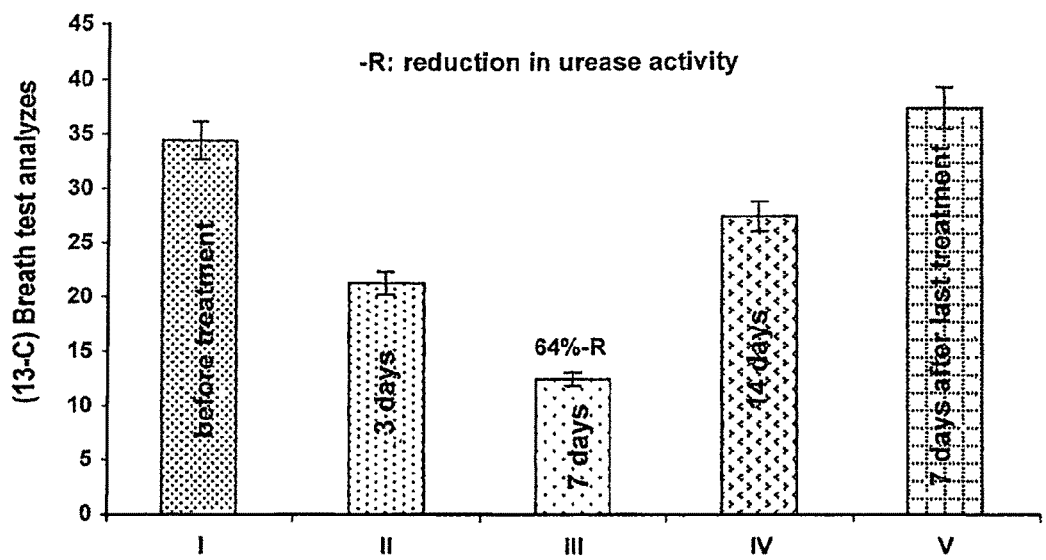
FIGS. 6A-F show results of treatment of human volunteers with drinkable fermented rye bran product. One patient and 5 volunteers with *H. pylori* infections were given the *L. curvatus*-fermented rye-bran product, iBran™, three times daily (see "Description of preferred embodiment"). The level of *H. pylori* infection was analyzed by 13C-urea breath test. Samples were collected during and after the entire treatment period, as indicated in the figure.
Figure 6B:
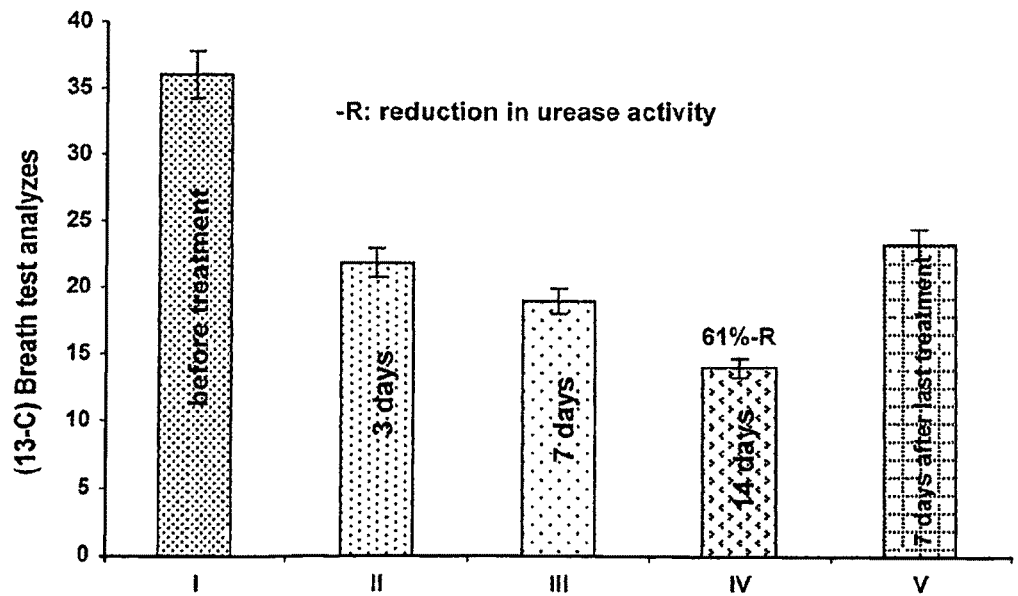
Figure 6C:
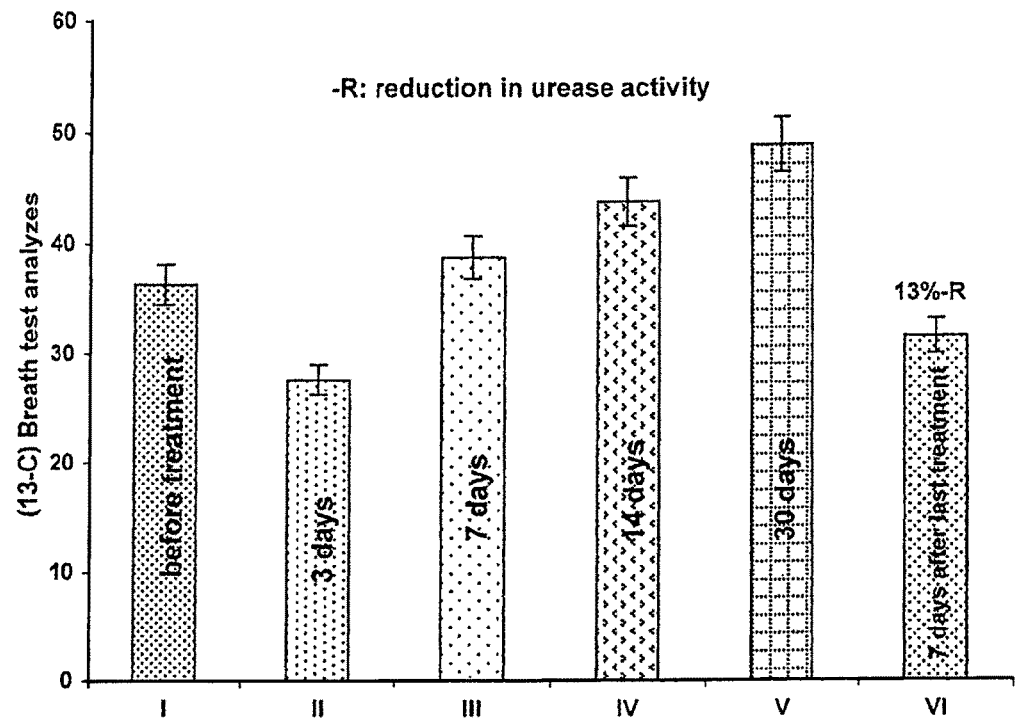
Figure 6D:
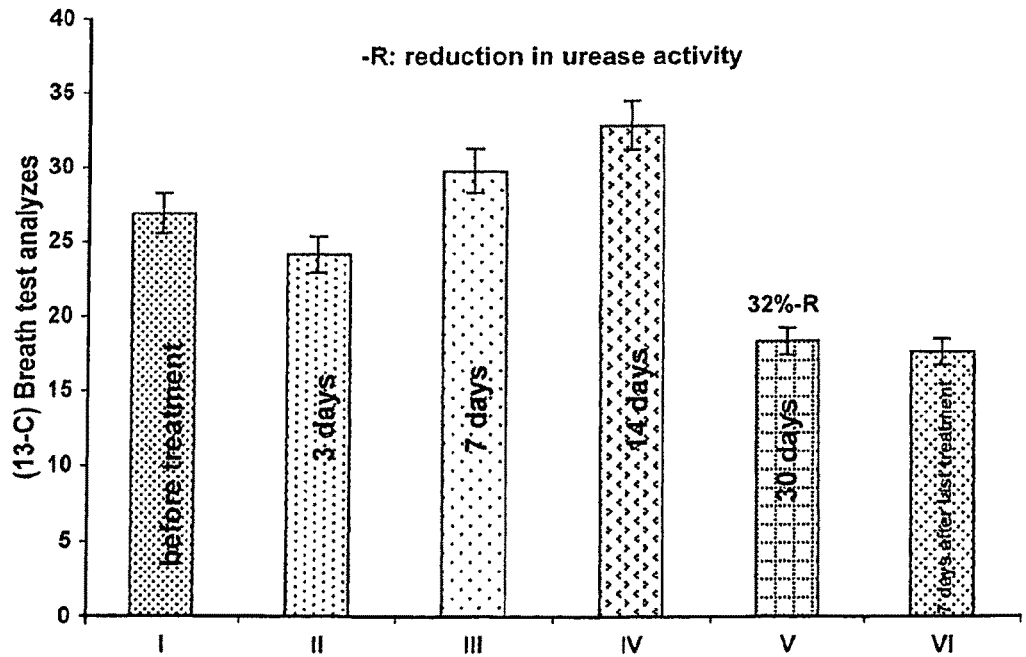
Figure 6E:
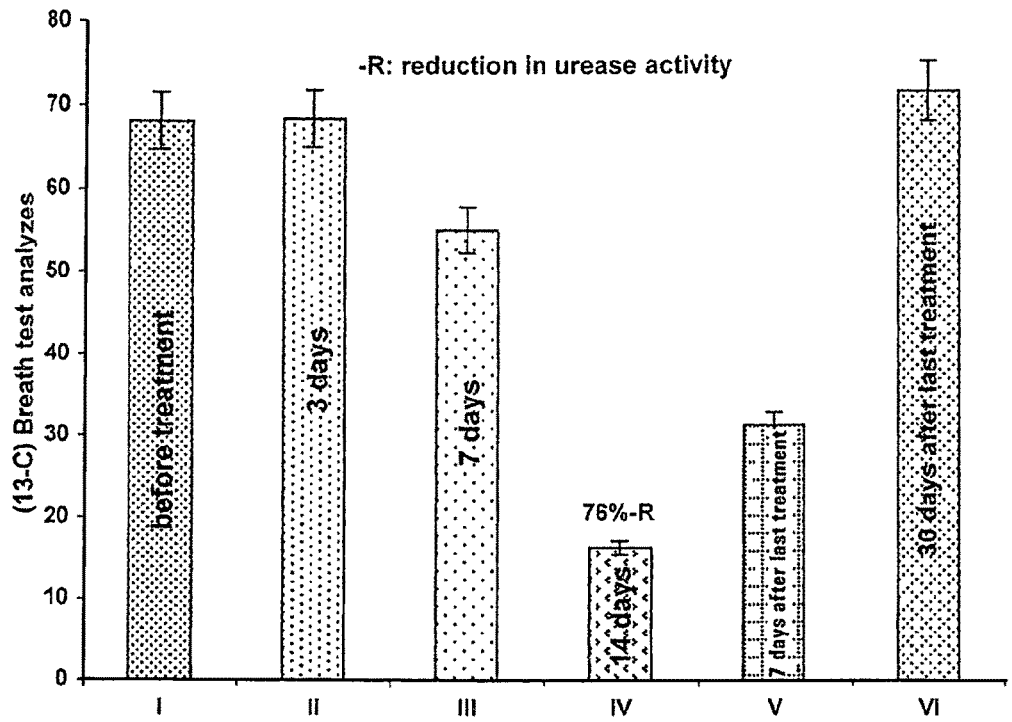
Figure 6F:
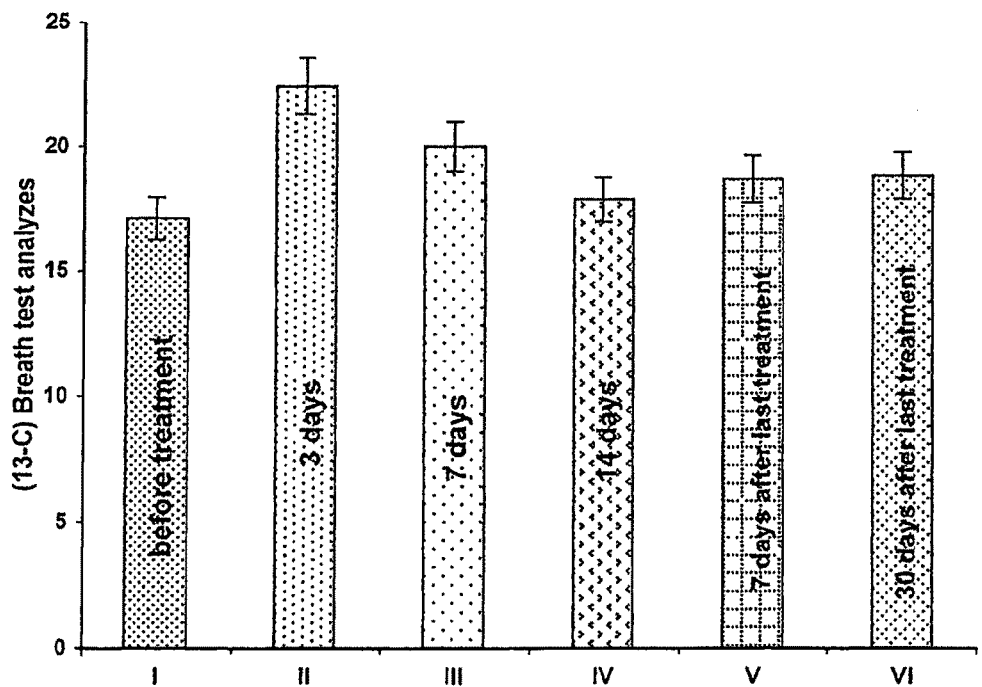

To analyze the thermo stabile properties of the anti-adhesive compounds of the fermented rye-bran product, and in addition to inactivate putative enzyme activities and/or thermo-labile. structures released during fermentation by L. curvatus, the product was boiled (at 100° C.) for 3 hours or autoclaved for 20, min, at 120° C. RIA analyzes showed that the fermented rye-bran product, with or without various heat treatments, inhibits H. pylori binding to the Lewis b antigen (FIG. 4). These results suggest that the rye-brain mediated inhibition activity did not result from degradation of the Lewis b antigen binding BabA adhesin protein by L. curvatus enzymes, such as proteases. Instead, the binding inhibitory activities could be due to receptor analogues or mimetics, released during the fermentation processes of the rye-bran.

Example 7

Pretreatment with Various Fermented Cereals

Several cereals (seeds and seed fractions) were studied for inhibition of H. pylori binding. When inhibition was plotted against bacterial density a relationship was found for most samples, indicating that an increased bacterial density in the extract results in an increased inhibition activity. L. curvatus-fermented rye-bran clearly demonstrates thy most efficient inhibition of *H. pylori* binding.

Example 8

Therapeutic Effect of the Fermented Rye-Bran Product, iBran™

One patient volunteer from Umea University Hospital with chronic active gastritis (clinical diagnosis was made by routine endoscopic and histological examinations), and in addition 5 healthy volunteers, were used in this study. The series of volunteers were first examined for the presence of gastric *H. pylori* by an urease test, *Helicobacter pylori* Urea-13C-breath test (Utandningstester i Sverige AB, Sweden), one week before treatment with fermented rye-bran. Positive volunteers were re-examined by the Urea-13C-breath test to calibrate and verify the start-value ("before treatment"-value), and the individual results demonstrated <5% variation in the 13C-breath analyzes. During the following two weeks period, the patients were given the fermented rye-bran according to the following protocol:

Samples of the fermented rye-bran were cultured and examined for detection of possible contaminants and was then, in addition, autoclaved before oral consumption. The rye-bran product was supplemented with 10% lingonberry juice and 10% glucose to improve the taste of the fermented beverage. Both supplements were first analyzed in vitro (by the Lewis b conjugate based RIA binding assay), to show no interference with the suppressing effect of rye-bran product on *H. pylori* adhesion. Dosage was 100 mL product, three times daily, corresponding to 300 mL/day fermented rye-bran for 2 weeks (see "Detailed Description of the Invention"). The patients were examined for the presence of gastric *H. pylori*, by the 13C-urease test during the entire treatment period (day 3, day 7, and day 14). In addition, two volunteers, in FIGS. 6 C and D, were given the product for 30 days and analyzed. Then, one week after the end of treatment and, in addition (FIGS. 6. A, B, E, F), and in addition, 30 days after end of treatment (FIGS. 6. C, D), the patient and the volunteers were examined for the presence of gastric *H. pylori* by the 13C-urease test. The results showed that the biological activity of the *H. pylori* infection decreased during therapy in a majority of individuals, but returns to the original level after the end of treatment.

Example 9

Inhibition Effect of the Fermented Rye-Bran and Other Fermented Cereals on *Candida albicans* and *Streptococcus mutans* Adherence

*Candida albicans* Adherence to Saliva-Treated Buccal Epithelial Cells

Human buccal epithelial cells were first mixed with parotid saliva (diluted 1:1 with PBS buffer). Then 250 µl ($2 \times 10^7$, cells/ml) of 35S-labeled *Candida albicans* cells were mixed with 250 µl ($1.75 \times 10^5$, cells/ml) of the saliva treated buccal epithelial cells, and finally, 250 µl of the various samples was added (one at the time), and incubated for 1 h in room temperature. Pre-treatment by the *L. curvatus*-fermented rye bran product (FIG. 7A, sample 2) reduced binding by Candida albicans to the saliva treated buccal epithelial cells, while many other cereals products had no effect, or even supported binding by *Candida albicans* (FIG. 7A).

*Streptococcus mutans* Adherence to Saliva-Treated Hydroxyapatite

Bacterial attachment to experimental salivary pellicles was measured by the "Hydroxyapatite assay". Adherence of [35S] methionine-labeled *Streptococcus mutans* bacteria ($5 \times 10^4$ to $15 \times 10^4$ cpm/ml; $1 \times 10^8$ bacteria/ml) to individual salivary protein samples adsorbed onto Hydroxyapatite beads (Fluka, Chemie AG, Buchs, Switzerland) was measured. So, unfractionated (whole) parotid saliva was adsorbed onto Hydroxyapatite beads (BHD Chemicals Ltd, Poole, UK) and subsequently incubated with $^{35}$S-metabolically labeled *S. mutans* bacteria (68 µl), together with an equal volume of the *L. curvatus* fermented rye bran product. Bacteria attached to the beads after two washes were determined by liquid scintillation counting. The rye bran product almost eliminated binding of *S. mutans* bacterial cells (FIG. 7B).

Example 10

Attenuation of Dextran Sodium Sulphate (DSS) Induced Colitis in Mice by Fermented Rye Product Introduction Dextran sulphate sodium (DSS) induced colitis is an experimental model of colonic inflammation in which the chemically caused epithelial damage to the colonic mucosa leads to a subsequent inflammatory reaction highly reminiscient of human colitis ulcerosa (Cooper et al. 1993). In order to study whether a fermented rye product can protect against colitis we have induced inflammation in mice by exposure to only DSS or to a mixture of DSS and said fermented rye product. In the experiment 3.5% (wt/vol) DSS was chosen as previous data from other laboratories (Okayasu et al. 1990, Cooper et al. 1993, Mahler et al. 1998) and our pilot study indicated that this concentration would lead to the development of acute colitis within 4-5, days of exposure enabling a good monitoring of the clinical symptoms.

Experimental Setup

Two groups of sex- and age matched mice, each group containing eight mice, where exposed to either 3.5% (wt/vol) DSS or a mixture of 3.5% (wt/vol) DSS and the fermented rye product in their drinking water ad libitum. All mice were monitored daily for the following clinical parameters, weight consistency of stools and rectal bleeding. The end-point of the analysis was day 10 or death earlier during the analysis period. The length of colon and small intestine was measured and tissue samples from proximal and distal small intestine, distal colon and spleen were collected for histology.

Results

Figure 8A:
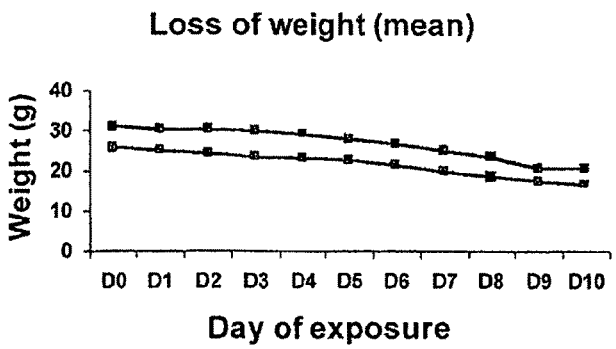
Figure 8B:
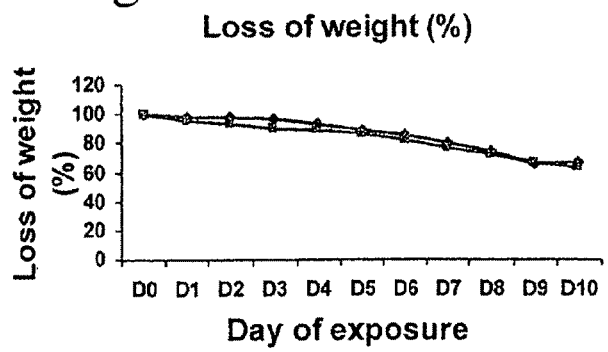
Figure 8C:
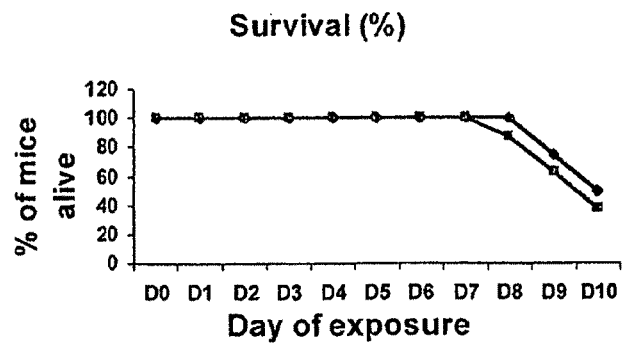
Figure 8D:
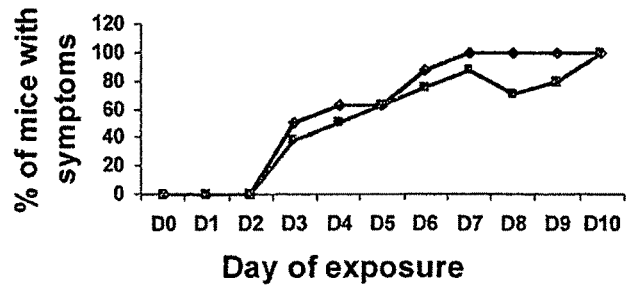
Figure 8E:
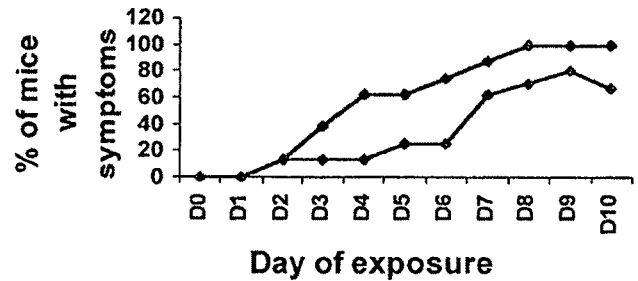
Figure 8F:
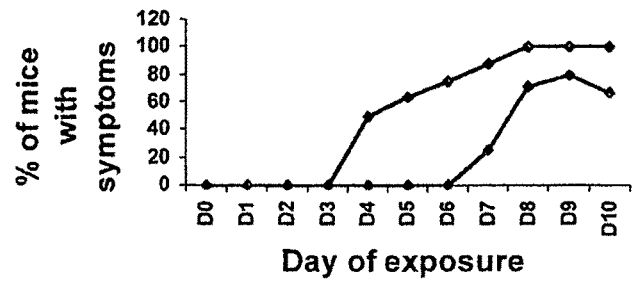

During the analysis period it became evident that both groups of mice displayed quite similar loss of weight (FIGS. 8A and B) as well as mortality (FIG. 8C). Epithelial damage was induced in both groups, which became clear by the similar time point of gross bleeding (FIG. 8D) observed in them. However, the mice receiving a mixture of DSS and the fermented rye product clearly displayed lower incidence of loose stools as well as diarrhea (FIGS. 8E and F). This indicates that the fermented rye product somehow can protect against these symptoms. We have also analyzed the histology of the distal colon by hematoxylin-eosin staining of tissue sections and have observed that the colitis in the mice receiving DSS and the fermented rye product is clearly milder than the mice exposed only to DSS (FIGS. 9 B and C).

CONCLUSION

The above findings indicate that the fermented rye product of the invention can attenuate the colitis in mice exposed to DSS. The implication may be that treatment with fermented rye bran also reduces inflammation in humans with intestinal inflammation such as ulcerative colitis, Crohn's disease.

SUMMARY

An activated product from a fermented cereal, preferably rye-bran fermented using *Lactobacillus curvatus*, demonstrates properties as an inhibitor of *H. pylori* adherence to the gastric epithelial mucosa. Thus, this novel anti-microbial strategy could possibly protect against oro-gastro-intestinal pathogens (OGIP), e.g. *Helicobacter pylori, Streptococcus mutans* and *Candida albicans* in humans, and oro-gastro-intestinal pathogens e.g., *Escherichia coli,* and *Clostridium perfringens*, in domestic animals, such as cattle, pig and poultry, and pet animals, such as dogs and cats. In addition, the invention refers to the stabilizing activity of the microbial flora as a supplemental growth promoting active feeding-stuff agent for animals such as pigs and chickens.

REFERENCES

1. Cover, T. L., Berg, D. E., Blaser, M. J., and Mobley, H. L. T. (2001), "*H. pylori* pathogenesis. In Principles of bacterial pathogensis", E. A. Groisman, ed. (New York, Academic Press), pp. 509-558.
2. H. Clausen and S. Hakomori, 1989, *Vox Sang,* 56, 1-20.
3. T. Borén, P. Falk, K. A. Roth, G. Larson and S. Normark, "Attachment of *Helicobacter pylori* to human gastric epithelium mediated by blood group antigens", *Science.* 262, 1892, 1993.
4. D. Ilver, A. Arnqvist, J. Ögren, I. M. Frick, D. Kersulyte, E. T. Incecik, D. E. Berg, A. Covacci, L. Engstrand and T. Borén, "*H. pylori* Adhesin Binding Fucosylated Histo-Blood Group Antigens Revealed by Retagging", *Science,* 279, 373-377, 1998.
5. M. Gehard, N. Lehn, N. Neumayer, T. Borén, R. Rad, W. Schepp, S. Miehlke, M. Classen and C. Prinz, "Clinical relevance of the *Helicobacter pylori* gene for blood-group antigen-binding adhesin", *Proc. Natl. Acad. Sci* USA, 96, 12778-12783, 1999
6. H. Miyabayashi, K. Furihata, T. Shimizu, I. Ueno, T. Akamatsu, "Influence of oral *Helicobacter pylori* on the success of eradication therapy against gastric *Helicobacter pylori*", *Helicobacter,* 5, 30-37, 2000.
7. M. Sadaka and A. Garcia, "Extraction of skimic and qucinic acids", *Chem. Eng. Comm.* 173, 91-102, 1999.
8. P. Falk, K. A. Roth, T. Borén, T. U. Westblom, J. I. Gordon and S. Normark, "An in vitro adherence assay reveals that *Helicobacter pylori* exhibits cell lineage-specific tropism in the human gastric epithelium", *Proc. Natl. Acad. Sci.* U.S.A., 90,2035, 1993.
9. Cooper H. S., Murthy S. N. S., Shah R. S. and Sedergran D. J. (1993): Clinico-pathologic study of dextran sulfate sodium experimental murine colitis. *Lab. Invest.* 69:238-249.
10. Mahler M., Bristol I. J., Leiter E. H., Workman A. E., Birkenmeier E. H., Elson C. O. and Sundberg J. P. (1998): Differential susceptibility of inbred mouse strains to dextran sodium-induced colitis. *Am. J. Physiol.* 274:G544-551.
11. Okayasu I., Hatakeyama S., Yamada M., Ohkusa T., Inagaki Y. and Nakaya R. (1990): A novel method in the induction of reliable experimental and acute chronic ulcerative colitis in mice. *Gastroenterology* 98:694-702.

The invention claimed is:

1. A fermented rye bran obtained by fermentation of rye bran with *Lactobacillus curvatus* strain Lb 14 DSMZ Deposit No. 13890, at 37° C. for about 24 hours, wherein said fermented rye bran is heat treated by heating the fermented rye bran at 100° C. for about 3 hours or by autoclaving at 120° C. for about 20 minutes, and is formulated as a food product suitable for human or animal consumption, and wherein said food product, upon consumption, inhibits the adherence and colonization of oro-gastro-intestinal pathogens (OGIPs) in humans and animals.

2. The fermented rye bran of claim 1, wherein said fermented rye bran comprises the supernatant of a fermentation broth obtained by fermentation of rye bran with *Lactobacillus curvatus* strain Lb 14 DSMZ Deposit No. 13890, at 37° C. for about 24 hours, wherein said fermented rye bran is heat treated by heating the fermented rye bran at 100° C. for about 3 hours or by autoclaving at 120° C. for about 20 minutes, and is formulated as a food product suitable for human or animal consumption, and wherein said food product, upon consumption, inhibits the adherence and colonization of oro-gastro-intestinal pathogens (OGIPs) in humans and animals.

3. The fermented rye bran of claim 2, wherein the food product is a beverage, bread, or muesli.

4. The fermented rye bran of claim 3, wherein the food product comprises lingonberry juice and glucose.

* * * * *